United States Patent [19]

Fekete

[11] 3,936,647
[45] Feb. 3, 1976

[54] X-RAY COLLIMATOR FOR CONTROLLING THE EMISSION OF SECONDARY RADIATION

[75] Inventor: Nicholas M. G. Fekete, Ellicott City, Md.

[73] Assignee: CGR Medical Corporation, Baltimore, Md.

[22] Filed: July 29, 1974

[21] Appl. No.: 492,842

Related U.S. Application Data

[63] Continuation of Ser. No. 357,241, May 4, 1973, abandoned.

[52] U.S. Cl. .............................. 250/512; 250/511
[51] Int. Cl.² ........................................... G21F 5/04
[58] Field of Search .................... 250/512, 511, 509

[56] References Cited
UNITED STATES PATENTS

| | | | |
|---|---|---|---|
| 2,722,611 | 11/1955 | Haupt | 250/512 |
| 2,844,736 | 7/1958 | Johns et al. | 250/512 |
| 3,163,762 | 12/1964 | Peyser | 250/512 |
| 3,193,408 | 7/1965 | Triller | 250/512 |
| 3,206,604 | 9/1965 | Burchell | 250/512 |
| 3,304,427 | 2/1967 | Peyser | 250/512 |
| 3,609,370 | 9/1971 | Peyser | 250/511 |
| 3,829,701 | 8/1974 | Hura | 250/511 |

Primary Examiner—James W. Lawrence
Assistant Examiner—B. C. Anderson
Attorney, Agent, or Firm—Brady, O'Boyle & Gates

[57] ABSTRACT

In an X-ray collimator including both "near" and "far" shutter mechanisms, the improvement comprising locating two pairs of independently movable near shutters within an outwardly extending lead cone. The cone is positioned against the X-ray generator tube window and as a result the near shutters are in closer proximity to the focal spot of a rotating anode disc of an X-ray tube than heretofore possible. The cone contains an aperture which defines the maximum size of the primary beam passing through the shutter mechanisms; however, the body of the cone and the closer positioning of the near shutters to the focal spot effectively controls and restricts secondary radiation which is emitted at angles different from the primary beam passing through the collimator.

11 Claims, 12 Drawing Figures

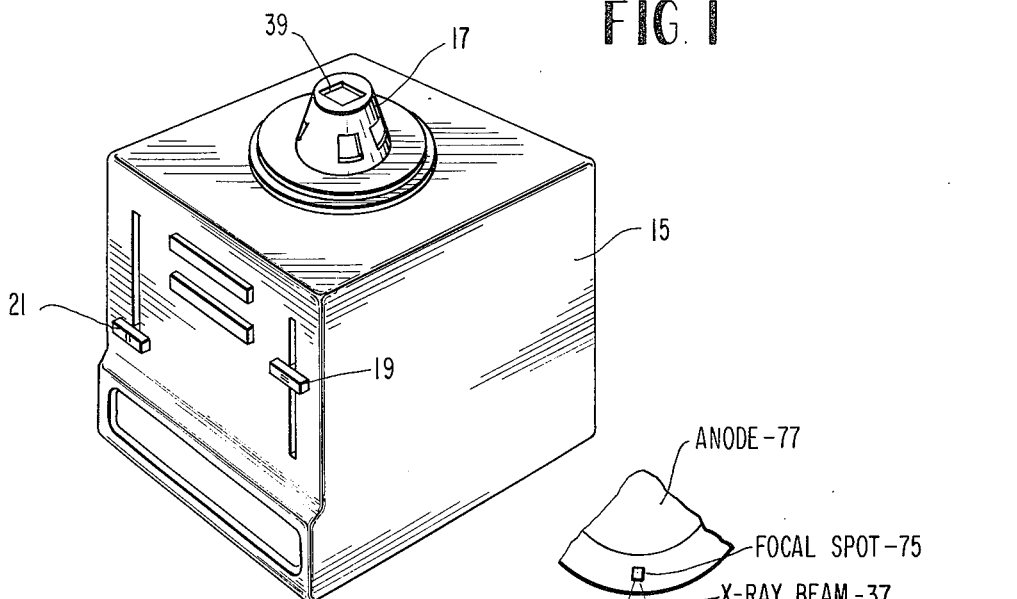
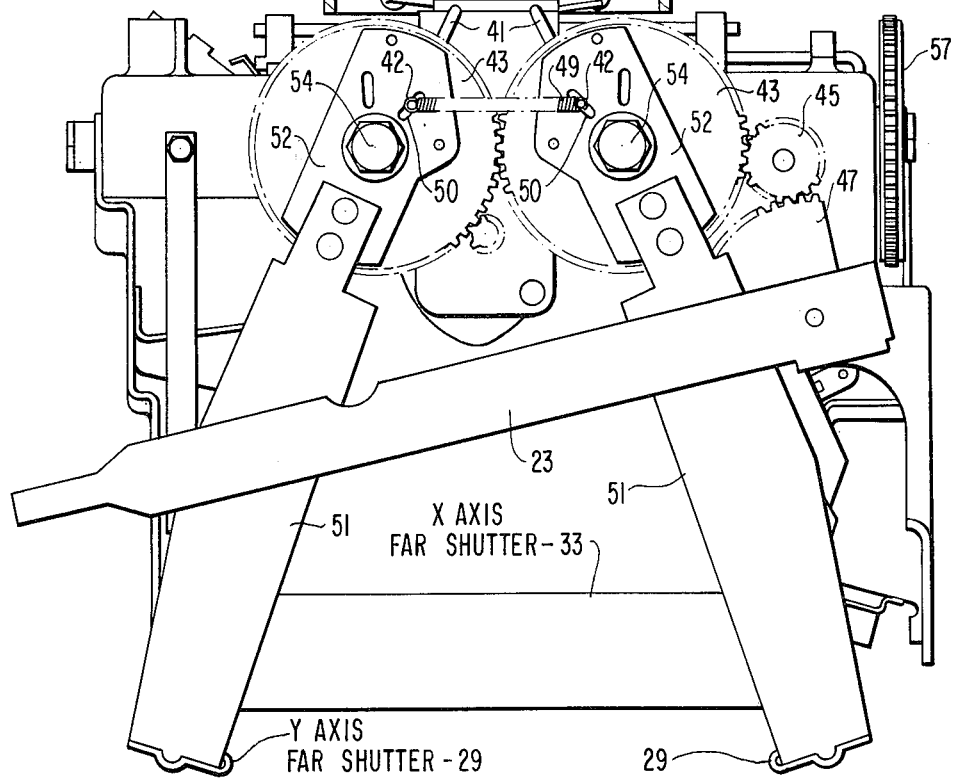

X-RAY COLLIMATOR FOR CONTROLLING THE EMISSION OF SECONDARY RADIATION

This is a continuation of application Ser. No. 357,241, filed May 4, 1973, now abandoned.

BACKGROUND OF THE INVENTION

1. Field of the Invention

This invention relates to collimating apparatus for controlling the shape and size of the beam of radiation such as an X-ray beam and more particularly for means for controlling secondary radiation in such apparatus.

2. Description of the Prior Art

For diagnosis and treatment of the human body, it is desirable to provide a beam of X radiation which impinges upon the subject only in a desired specific location and which is confined to the specific area of interest. To this end, collimating devices utilizing one or more sets of adjustable shutters are utilized. Such apparatus is well known to those skilled in the art.

In an X-ray generating tube, a beam of electrons is directed or focused towards a small area or focal spot on a rotating anode disc. For various physical phenomenon, the focusing of this beam of electrons is not achieved completely. As a result, X-rays are generated and emitted not only from the desired focal spot, but also from other peripheral areas of the anode disc as well as from some of the disc mounting parts, e.g. the stem and retaining nut. Thus in practice, secondary radiation often referred to as off focus radiation, is emitted from all X-ray generating tubes at angles different from the primary beam.

U.S. Pat. No. 2,722,611 issued to W. H. Haupt, discloses a collimating apparatus of the type described, and additionally includes a cone which is located between the X-ray tube head and the shutter mechanism. However, to effectively control and restrict the emission of secondary radiation, it is imperative that the geometrical location of the near shutters in a double tier shutter mechanism, be located as close to the focal spot as physically permissible. In attempting such an arrangement, however, the physical space limitations of prior art apparatus results in undesirable amounts of secondary radiation passing through the restricting shutter mechanisms.

SUMMARY

Briefly, the subject invention is directed toward a double shutter collimating device having a housing which is adapted to be located contiguous with or in relatively close proximity to an X-ray generating tube. The housing has a lead cone projecting outwardly therefrom toward the focal spot of the X-ray tube anode and has a rectangular aperture in its narrow end wall which defines the maximum size of the primary beam. Two pairs of near shutters, one for the X axis and one for the Y axis, are positioned within the lead cone and are independently movable therein so as to position the near shutters relatively closer to the tube's focal spot than heretofore possible. Thus the near shutters appropriately envelop the primary beam immediately after it enters the aperture in the lead cone, thereby eliminating much of the secondary radiation which is emitted at angles different from the primary beam. Additionally, the lead cone provides a physical protection against damage of the relatively delicate and highly accurately positioned near shutters.

BRIEF DESCRIPTION OF THE DRAWINGS

FIG. 1 is a perspective view of the collimator apparatus forming the subject invention;

FIG. 2 is a side elevational view primarily showing in detail the pair of Y axes near shutter elements in the fully open position within a lead cone as well as the operating mechanism for the Y axis shutters;

DESCRIPTION OF THE PREFERRED EMBODIMENT

Figure 3:
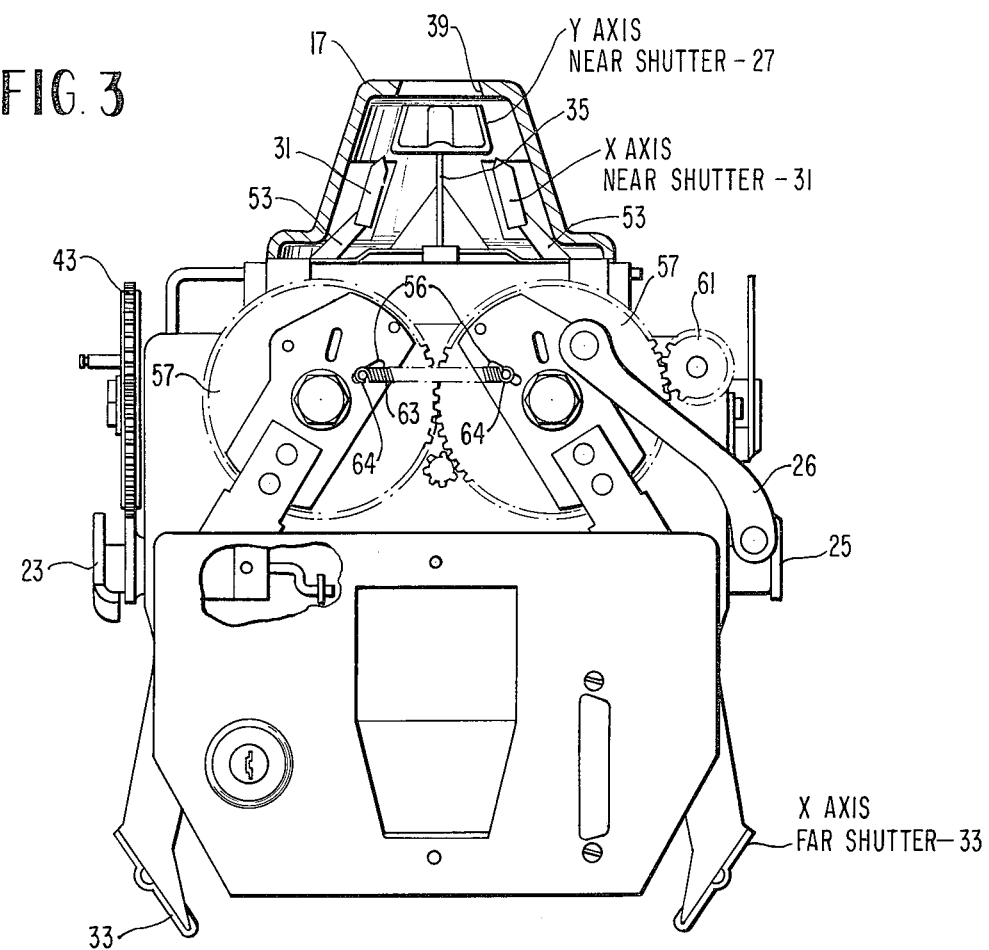
FIG. 3 is a front elevational view primarily illustrating in detail the pair of X axes near shutter elements in a fully open position within the lead cone and the operating mechanism therefor.

Referring now to the drawings wherein like numerals refer to like parts in the various figures, FIG. 1 is illustrative of a collimator housing 15 which is adapted to contain the shutter operating mechanisms shown in detail in FIGS. 2 and 3. The housing 15 has a lead cone 17 fixed thereto which is adapted to be contiguously positioned against the window 18 of an X-ray generating tube partially shown in FIG. 2. A pair of finger gripping means 19 and 21 (FIG. 1) are attached to levers 23 and 25 shown in FIGS. 2 and 3 respectively. Lever 23 is adapted to manually change the opening and closing of a pair of near shutters 27 and a pair of far shutters 29 along one orthogonal axis of movement referred to as the Y axis. The lever 25, on the other hand, in combination with a crank 26 shown in FIG. 3 is adapted to simultaneously open and close a pair of near shutters 31 and a pair of far shutters 33 along the other othogonal axis referred to as the X axis. The two pairs of near shutters 27 and 31 comprise what is referred to in the art as plate shutters and project upwardly in an inclined fashion inside of the lead cone 17 with the Y axis near shutters 27 being located above the X axis near shutters 31. Thus one pair of shutters will be freely movable independently of the other inside of the cone without mutual interference. The shutter elements have generally trapezoidal faces, one X axis near shutter 31 being shown in detail in FIG. 2, and one Y axis near shutter 27 being shown in FIG. 3.

Figure 4:
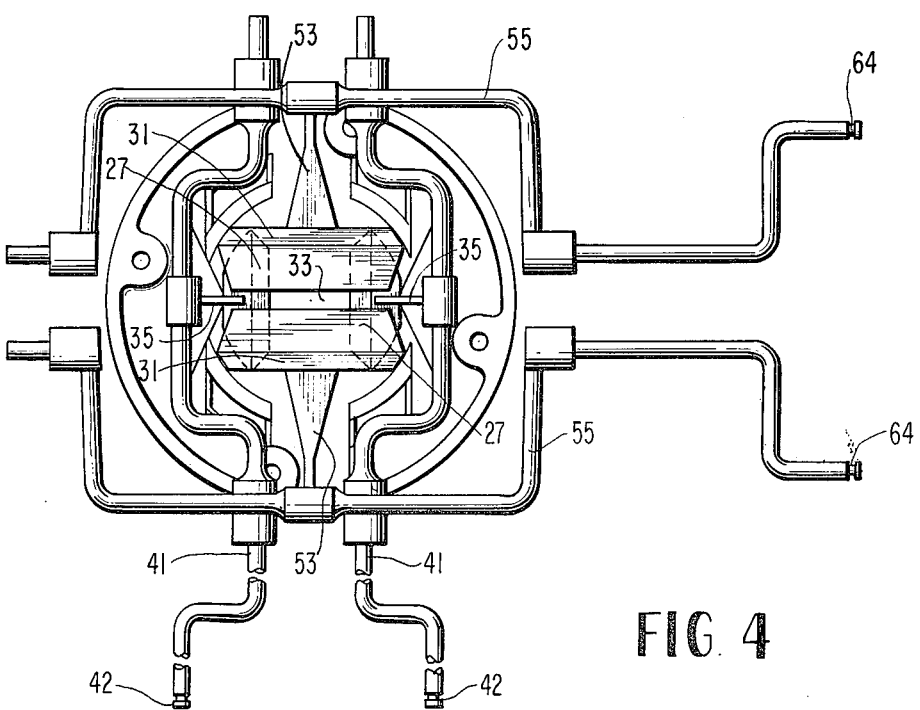
FIG. 4 is a bottom view of the two pairs of near shutters for the X and Y axes as well as the respective control arms therefor.

Referring now briefly to FIG. 4, the interrelation of the two pairs of near shutters 27 and 31 define a rectangular opening 33 the size of which is determined by the mutual separation of the near shutter elements. The shutter elements are adapted to be moved in the following manner. Considering first the upper, i.e. the Y axis near shutters 27, reference is made particularly to FIGS. 2 and 4. The shutter elements 27 are attached to projecting finger elements 35 which incline upwardly inside of the lead cone 17 in the vicinity of the inner wall so as to permit an unobstructed passage of an X-ray beam 37 except for that provided by the rectangular aperture 39 in the lead cone 17 and the shutter elements. The finger elements 35 are rigidly attached to the eccentric portion of a pair of crank shafts 41 (FIG. 4) which in turn are connected at their terminal ends 42 to a gear train comprised of the spur gears 43, 45, 47 (FIG. 2). The partial gear 47, in turn, is connected to the lever 23. A tension spring 49 innerconnects the terminal ends 42 of the crank portion of the shafts 41 projecting through the slot 50 of gear 43 for applying a bias thereto and urges the fingers 35 and the shutter elements 27 mutually outwardly. It can be seen by reference to FIG. 2, that an up-down movement of the lever 23 will cause rotation of the spur gears 43 which will in turn cause movement of the crank shafts 41 thereby moving the shutter elements toward or away from each other depending upon the rotational direction of the gear train.

Figure 8:
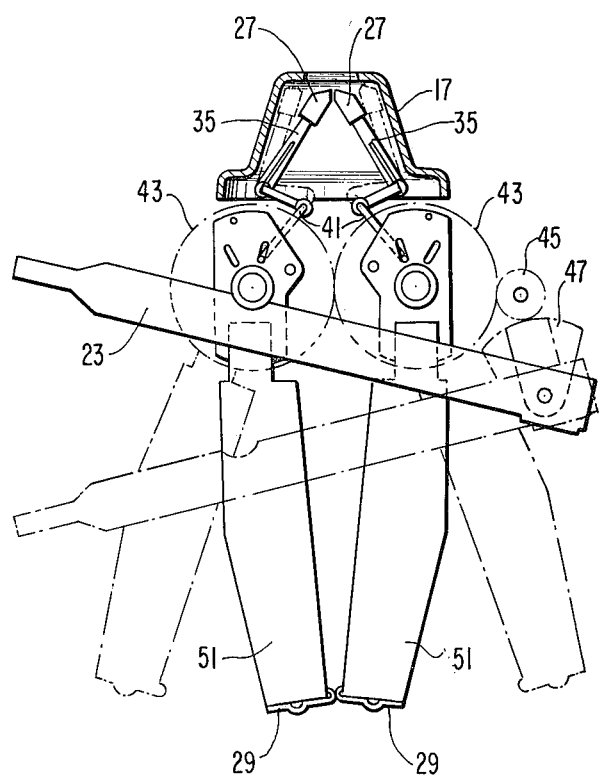
FIG. 8 is a partial side elevational view illustrative of the unitary operating mechanism for both near and far shutters of the Y axis.

Regarding the far shutter elements 29 for the Y axis, they are attached to downwardly extending elements 51 which are secured to a plate 52 mounted on the gear 43 by means of the nut 54. Thus any movement of the near shutter elements 27 is also accompanied by a corresponding movement of the far shutter elements 29. This is further illustrated in FIG. 8 which discloses the Y axis shutters in a closed position while the phantom lines disclose the fully open position.

The X axis near shutters 31 operate in substantially the same manner. Referring now to FIGS. 3 and 4, the shutter elements 31 are attached to upwardly projecting finger elements 53 which in turn are connected to crank shafts 55 which are disposed normally to the crank shafts 41 and project through the slot 56 in the spur gear 57, one of which is connected by means of the member 26 to the lever 25. A spur gear 61 which is similar to the gear 45 shown in FIG. 2, also couples to the same gear 57 attached to the member 26. Both gears 45 and 61 are coupled to slip clutches, not shown, for providing motorized operation of the shutter mechanisms when desirable. Also as before, a tension spring 63 is attached to both ends 64 (FIG. 4) of the control arms 55 for biasing the shutters mutually outwardly toward the inner wall surface of the lead cone 17.

Figure 5:
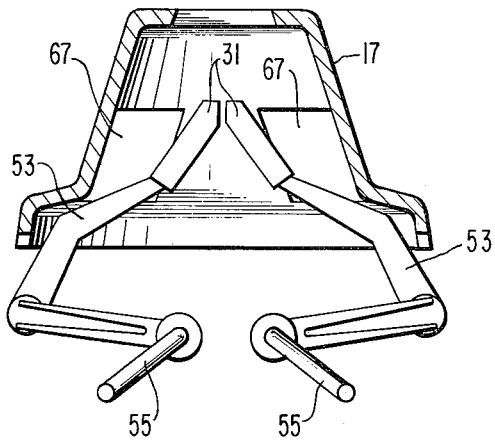
FIG. 5 is a partial front elevational view illustrative of the X axis near shutters in a substantially fully closed position within the lead cone.
Figure 6:
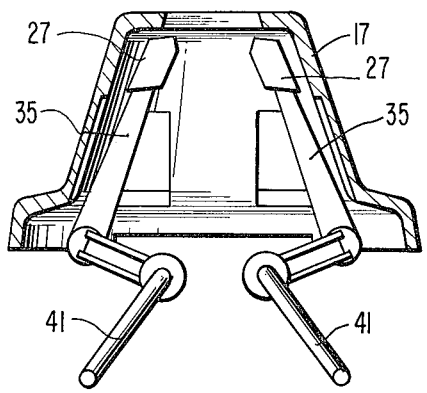
FIG. 6 is a partial side elevational view illustrative of the Y axis near shutters in a substantially fully open position.
Figure 7:
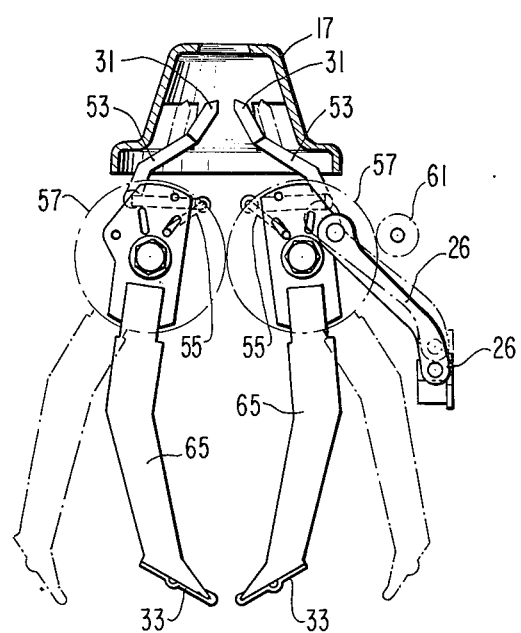
FIG. 7 is a partial front elevational view illustrative of the unitary operating mechanism for both the near and far shutters of the X axis.

Referring now to FIG. 5, this figure discloses the details of the physical configuration of the finger elements 53 and the control arms 55 which move the shutter elements 31 in mutual relation to one another independently of the other pair of shutter elements 27. FIG. 7 further discloses the manner in which both the near shutter elements 31 and the far shutter elements 33 for the X axis move simultaneously due to the downwardly projecting members 65 coupled to the gears 57. The configuration of FIG. 7 discloses the shutter mechanism for the X axis being in a partly closed position by a downward movement of the member 26 in response to an upward movement of the lever 25 which would in turn be caused by pushing the finger grip 21 as shown in FIG. 1, up. The phantom view of FIG. 7 discloses the shutter mechanism being in a partly open position.

It should now be observed that the length of the X axis near shutters 31 is relatively greater than the corresponding length of the Y axis near shutters 27 as evidenced by FIG. 4. This can also be shown by noting the length of the X axis near shutter 31 shown in FIG. 2 with respect to the Y axis near shutter 27 shown in FIG. 3. The relative dimensions of the near shutter elements 27 and 31 stems from the fact that the X axis near shutters 31 are positioned below the Y axis near shutters 27 within the lead cone 17.

Figure 9:
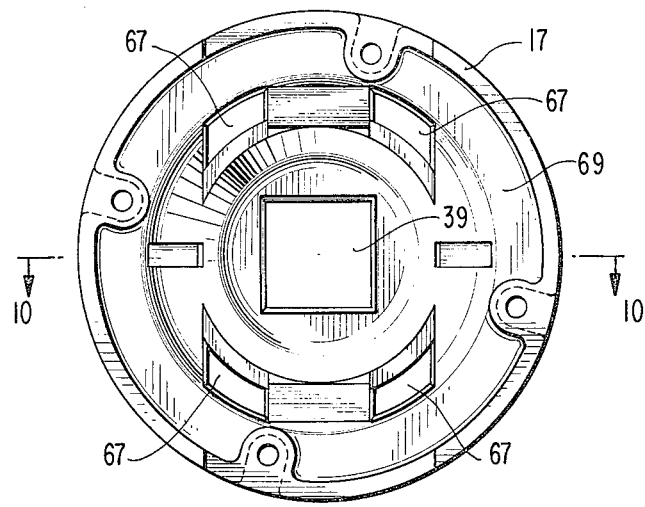
FIG. 9 is a bottom view of the lead cone of the subject invention.
Figure 10:
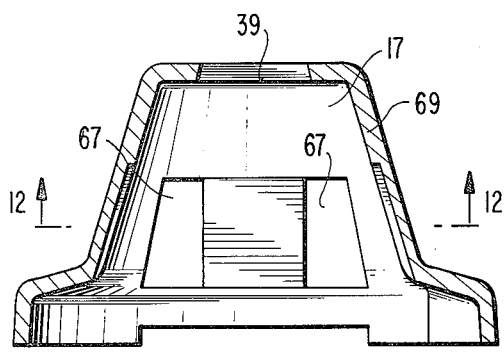
FIG. 10 is a cross sectional view of the lead cone shown in FIG. 9 taken along the lines 10-10 thereof.
Figure 11:
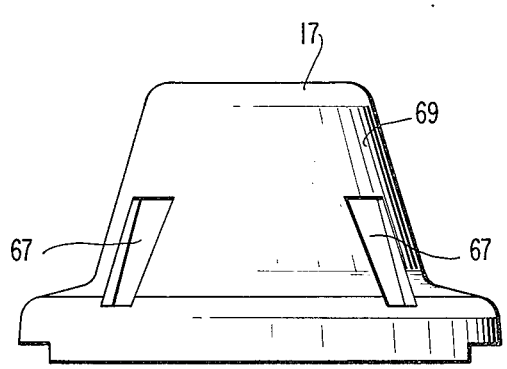
FIG. 11 is an elevational view further illustrative of the lead cone.
Figure 12:
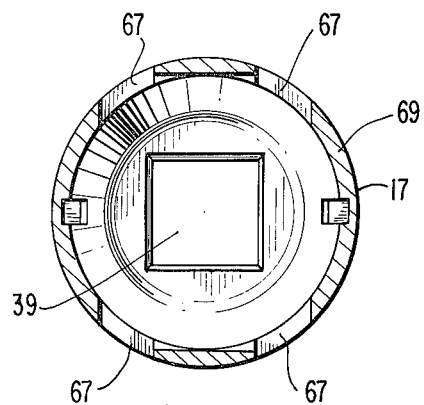
FIG. 12 is a cross sectional view of the lead cone shown in FIG. 10 taken along the lines 12—12 illustrating the rectangular aperture for the passage of the primary beam.

It will be appreciated that the outward movement of the X axis near shutter elements 31 would be unnecessarily restricted by certain portions of the inner wall surface of the lead cone 17. To facilitate the movement of the X axis near shutter elements 31 to selected open positions as well as the maximum or fully open position desirable, four apertures 67 are provided, one for each outer edge of the two elements 31 in the body of the cone 17 shown in detail in FIGS. 9 through 12. FIG. 9 illustrates that two apertures are provided on each side of the sloping body portion 69 in the lower half section thereof. The size of the apertures 67 are determined by the physical requirements dictated by the size of the shutter elements 31 and the maximum amount of outward travel defined by the fully open position.

The collimator apparatus as disclosed in the various figures is adapted to be located with respect to the X-ray generator tube such that the lead cone 17 abuts the X-ray window 18 contained in a tube housing shown in fragmentation by reference numeral 73 in FIG. 2. The window 18 is shown being concave in configuration permitting the X-ray beam 37 emanating from a focal spot 75 to pass therethrough. This is a typical configuration for conventional X-ray generating tubes used in combination with collimating devices. It can be seen by reference to FIG. 2, that the collimator having the lead cone 17 including the near shutter elements 27 and 31 contained therein, projects into the cup shaped window 71 permitting the near shutters to be placed relatively closer to the focal spot 75 than heretofore possible.

Secondary radiation or off focus radiation as it is sometimes referred to, constitutes radiation which is emitted at different angles than the primary beam emanating from the focal spot. For example, referring to FIG. 2, the primary beam is shown as the beam 37. The secondary radiation are X-rays generated and emitted from other peripheral areas of the anode 77 as well as from mounting parts, not shown. It can be seen, therefore, that the lead cone 17 not only itself limits secondary radiation by providing a shielding effect but more importantly the immediate proximity of the near shutter elements 27 and 31 to the square aperture 39 in the end of the cone envelope the primary beam at the aperture 39 preventing most of the secondary radiation from passing through to the far shutters 29 and 33 which has not already been restricted by the shielding action of the cone itself. Thus the combination of the lead cone and the near shutter mechanisms for both the X and the Y axis being located within the lead cone provides improved means for eliminating the undesirable secondary radiation which is inherent in present day X-ray generating tubes.

Having shown and described what is at present considered to be the preferred embodiment of the invention, I claim:

1. X-ray collimator apparatus comprising in combination:
   a collimator housing having a central axial opening therethrough adapted for the passage of an X-ray beam therethrough and additionally including actuator means for selectively controlling the movement and position of near and far shutter means for controlling the shape and size of an X-ray beam transmitted to a target area from an X-ray generator, said X-ray generator having a window of predetermined shape for the passage of said X-ray beam therethrough;
   an outwardly projecting lead cone type shield member impervious to X-rays located between the near shutter means and the focal spot of said X-ray generator, said shield member including an aperture in substantial alignment with said X-ray beam adjacent said window, the size of said aperture defining the maximum size of the X-ray beam permitted to enter and pass through said collimator housing, said shield member being further adapted to envelop as well as protect the near shutter means, being attached to the top of said collimator housing over said opening and having a shape substantially conforming to the shape of said window thereby confining secondary or off-focus radiation emitted from said X-ray generator and permitted to enter said collimator housing entirely to said aperture;
   a first and second pair of adjustable near shutters, comprising said near shutter means, coupled to said actuator means and comprising blade shutter elements for respective orthogonal axes, both pairs of near shutters being located entirely within said shield member adjacent said aperture and being adapted for mutually independent non-obstructed movement therein for not only defining the desired shape and size of the X-ray beam by movement past the boundary of said aperture into the open space provided thereby to intersect the X-ray beam, but also more effectively confining and restricting said secondary radiation present at said aperture, said confining being accomplished by the relatively closer positioning of said near shutter pairs to said window and said aperture and accordingly to the focal spot of said X-ray generator whereby an additional shielding effect is provided by the shutters themselves due to the movement of said near shutters past the boundary of said aperture, said first pair of shutter means being relatively smaller in size than said second pair of shutters and having a respective leading edge located immediately adjacent said aperture while said second pair of shutters is located immediately below said first pair of shutters and having a respective leading edge orthogonal to the leading edges of said first pair of shutters; and
   means coupled to said actuator means for selectively providing manual and motor driven operation of said shutters.

2. The apparatus as defined by claim 1 and additionally including a first and second pair of adjustable far shutters, comprising said far shutter means, located in said collimator housing and being coupled to said actuator means for being operated in conjunction with respective pairs of said first and second pairs of near shutters.

3. The apparatus as defined by claim 1 wherein said shield member comprises a generally frusto conical member having a relatively smaller end including a wall, a side wall, and a larger end open inwardly toward said collimator housing opening, said aperture being located in the smaller end wall.

4. The apparatus as defined by claim 3 wherein said shield member includes a plurality of openings in the side wall for permitting predetermined outward movement of said one pair of near shutters.

5. The apparatus as defined by claim 4 wherein said shield member is comprised of lead.

6. The apparatus as defined by claim 4 wherein said shield member comprises a flanged conical member comprised of lead having a generally flat smaller end wall containing said aperture, said aperture being generally centered in the longitudinal axis of said X-ray beam.

7. The apparatus as defined by claim 6 wherein said aperture comprises a rectangular opening.

8. The apparatus as defined by claim 7 wherein said near blade shutter elements comprise a first and second pair of opposed shutter plates and wherein said pairs of shutter plates are selectively positioned in close proximity to the inner wall of said conical member.

9. The apparatus as defined by claim 1 wherein said actuator means comprises a first and second individually driven gear train mounted in said housing, and additionally including coupling means from said near shutter means thereto comprising a finger element attached to a respective shutter blade element, said finger element inclining upwardly inside of said shield member in the vicinity of the inner side wall thereof to permit unobstructed passage of said X-ray beam thereby, and a respective angulated offset control arm linkage member connecting said shutter blade to its respective gear train.

10. The apparatus as defined by claim 1 wherein said actuator means comprises:
   a first and second spur gear assembly mutually arranged in generally orthogonal planes within said collimator housing for respectively driving said first and second pairs of near shutters, each gear assembly including at least two meshed driven spur gears of relatively equal diameter;
   a first pair of crank shafts, each having an eccentric portion and a crank portion, parallely arranged on a first level in the upper portion of said collimator housing with said eccentric portion thereof disposed around and mutually outwardly from the central axis of said housing to permit said X-ray beam to pass unobstructed therethrough and with said crank portion directed toward and coupled to a respective spur gear of said two spur gears of said first gear assembly;
   a first and second finger element inclining upwardly inside of said shield member in the vicinity of the inner side wall thereof respectively coupling the eccentric portion of said first pair of crank shafts to said first pair of near shutters;
   a second pair of crank shafts, each having an eccentric portion and a crank portion, parallely arranged normal to said first pair of crank shafts and being located on the second level in the upper portion of said collimator housing with said eccentric portion thereof also disposed mutually around and outwardly from the central axis of said housing to permit said X-ray beam to pass unobstructed therethrough and with said respective crank portion directed toward and coupled to a respective spur gear of said two spur gears of said second gear assembly; and
a third and fourth finger element inclining upwardly inside of said shield member in the vicinity of the inner side wall thereof respectively coupling the eccentric portion of said second pair of crank shafts to said second pair of near shutters.

11. The collimator as defined by claim 10 wherein said two spur gears of said first and second spur gear assembly each includes a slot therethrough located intermediate the center and periphery thereof for receiving the terminal end of the crank portion of the respective crank shaft coupled thereto; and a tension bias spring member connected between the crank portion terminal ends of respective pairs of crank shafts for biasing said pairs of near shutters outwardly from the central axis of said housing.

* * * * *